(12) United States Patent
Matsui et al.

(10) Patent No.: US 8,722,719 B2
(45) Date of Patent: May 13, 2014

(54) AMINE COMPOUND AND USE FOR SAME

(75) Inventors: Ryo Matsui, Tokyo (JP); Toru Yamazaki, Tokyo (JP); Shigeyuki Kikumoto, Tokyo (JP)

(73) Assignee: Kureha Corporation, Tokyo (JP)

( * ) Notice: Subject to any disclaimer, the term of this patent is extended or adjusted under 35 U.S.C. 154(b) by 0 days.

(21) Appl. No.: 13/878,131

(22) PCT Filed: Sep. 30, 2011

(86) PCT No.: PCT/JP2011/072563
§ 371 (c)(1),
(2), (4) Date: May 22, 2013

(87) PCT Pub. No.: WO2012/046653
PCT Pub. Date: Apr. 12, 2012

(65) Prior Publication Data
US 2013/0245280 A1  Sep. 19, 2013

(30) Foreign Application Priority Data

Oct. 6, 2010  (JP) .................................. 2010-226370

(51) Int. Cl.
*A61K 31/4178* (2006.01)
*C07D 403/12* (2006.01)

(52) U.S. Cl.
USPC ...................................... 514/397; 548/312.7

(58) Field of Classification Search
USPC ...................................... 514/397; 548/312.7
See application file for complete search history.

(56) References Cited

U.S. PATENT DOCUMENTS

| | | | |
|---|---|---|---|
| 7,176,227 B2 | 2/2007 | Hirose et al. | |
| 7,833,991 B2 | 11/2010 | Yamazaki et al. | |
| 7,932,281 B2 | 4/2011 | Saitou et al. | |
| 2007/0208007 A1 | 9/2007 | Saitou et al. | |
| 2011/0172212 A1 | 7/2011 | Saitou et al. | |

FOREIGN PATENT DOCUMENTS

| | | |
|---|---|---|
| WO | 2004/024697 | 3/2004 |
| WO | 2005/085209 | 9/2005 |

OTHER PUBLICATIONS

International Search Report for PCT/JP2011/072563 dated Nov. 29, 2011.
International Preliminary Report on Patentability of PCT/JP2011/072563 dated May 16, 2013.

*Primary Examiner* — Samantha Shterengarts
(74) *Attorney, Agent, or Firm* — Greenblum & Bernstein, P.L.C.

(57) ABSTRACT

Provided is an ester of 3-[(4-dipropylamino-butyl)(4-{[(1H-imidazole-2-ylmethyl)(1-methyl-1H-imidazole-2-ylmethyl)amino]methyl}benzyl)amino]propionic acid which is easily hydrolyzed in serum. The amine compound of the present invention is an ester compound represented by general formula (1). (In general formula (1), n is 1-4, and $R_1$ and $R_2$ represent an alkyl group having 1-3 carbon atoms.)

(1)

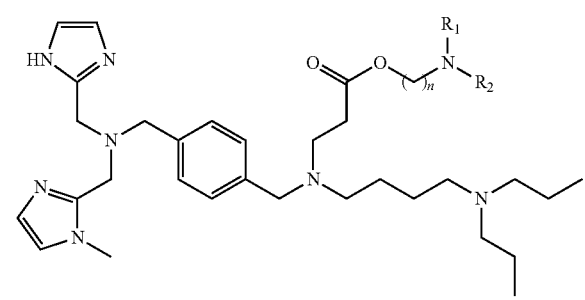

11 Claims, No Drawings

AMINE COMPOUND AND USE FOR SAME

TECHNICAL FIELD

The present invention relates to an amine compound that has antiviral activity based on antagonism against a chemokine receptor CXCR4.

BACKGROUND ART

It is known that HIV-1 infects cells one after another via CXCR4 as a coreceptor. Therefore, a compound that functions as an appropriate CXCR4 antagonist can prevent infection of HIV-1, and may be used as an anti-HIV-1 agent that has a novel action mechanism.

The applicant of the present application found 2-([4-(dipropylamino)butyl]{[4-({[(1H-imidazol-2-yl)methyl][(1-methyl-1H-imidazol-2-yl)methyl]amino}methyl)phenyl]methyl}amino)acetic acid tri-(2R,3R)-tartrate (see the following formula (1)) as a novel CXCR4 antagonist (see Patent Documents 1 and 2).

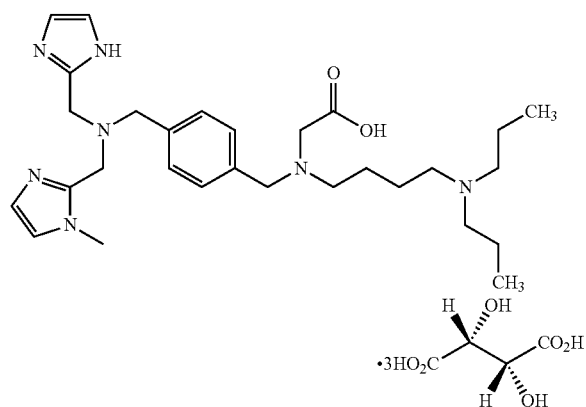

(1)

The compound represented by the formula (1) is effective against HIV-1, and is expected to be used as a drug that exhibits low toxicity and has few side effects.

RELATED-ART DOCUMENT

Patent Document

[Patent Document 1] WO2004/024697
[Patent Document 2] WO2005/085209

SUMMARY OF THE INVENTION

Technical Problem

However, some of the compounds disclosed in Patent Documents 1 and 2 have the following problems. For example, 3-[(4-dipropylaminobutyl)(4-{[(1H-imidazol-2-ylmethyl)(1-methyl-1H-imidazol-2-ylmethyl)amino]methyl}benzyl)amino]propionic acid (hereinafter may be referred to as "compound A") represented by the formula (1) exhibits excellent CXCR4 antagonism, but exhibits poor oral absorption properties. Therefore, it is preferable to chemically modify part of the compound A to improve oral absorption properties in order to utilize the compound A as an oral drug.

Patent Document 2 discloses an ethyl ester of the compound A. However, the inventors of the present invention found that the ethyl ester of the compound A is hydrolyzed to only a small extent in serum. When an ester of the compound A is not hydrolyzed in serum, the ester of the compound A may be accumulated in the body of the subject, for example, and may have unexpected side effects or toxicity.

The present invention was conceived in view of the above problems. A main object of the present invention is to provide an ester of 3-[(4-dipropylaminobutyl)(4-{[(1H-imidazol-2-ylmethyl)(1-methyl-1H-imidazol-2-ylmethyl)amino]methyl}benzyl)amino]propionic acid, which is easily hydrolyzed in serum.

Solution to Problem

The inventors of the present invention conducted extensive studies in order to achieve the above object. As a result, the inventors found that an ester of the above compound produced using an alcohol that includes a dialkylamine is easily hydrolyzed in serum, and this finding has led to the completion of the invention. The inventors also found that an ester of the above compound produced using an alcohol that includes a dialkylamine exhibits anti-HIV activity equivalent to that of the hydrolyzed compound (compound A). The present invention was achieved based on the above novel findings, and includes the following aspects.

An amine compound according to the present invention is represented by the following general formula (2).

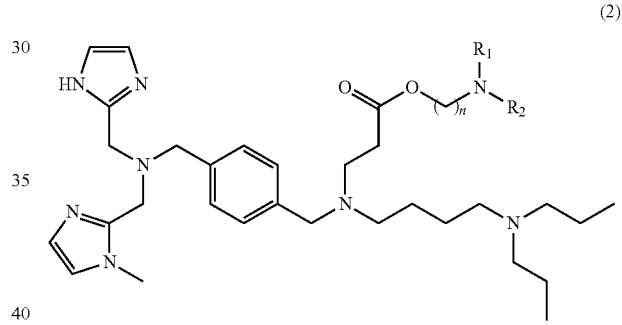

(2)

wherein n is an integer from 1 to 4, and $R_1$ and $R_2$ represent an alkyl group having 1 to 3 carbon atoms.

In the amine compound according to the present invention, it is preferable that n in the general formula (2) is 2 or 3.

In the amine compound according to the present invention, it is preferable that n in the general formula (2) is 2, and $R_1$ and $R_2$ in the general formula (2) represent a methyl group or an ethyl group.

The amine compound according to the present invention is preferably 2-dimethylaminoethyl 3[(4-dipropylaminobutyl)(4-{[(1H-imidazol-2-ylmethyl)(1-methyl-1H-imidazol-2-ylmethyl)amino]methyl}benzyl)amino]propionate.

A pharmaceutical composition comprising as an active ingredient the amine compound according to the present invention, and a pharmaceutical composition comprising as a prodrug the amine compound according to the present invention are also included within the scope of the present invention.

A CXCR4 antagonist, an antiviral drug, an anti-rheumatic disease agent, and an anti-metastatic disease agent comprising as an active ingredient the amine compound according to the present invention as an active ingredient are also included within the scope of the present invention.

A pharmacologically acceptable salt of the amine compound represented by the general formula (2) is also included within the scope of the present invention. The pharmacologically acceptable salt of the amine compound according to the present invention is preferably a salt of citric acid.

Advantageous Effects of the Invention

The amine compound according to the present invention is easily hydrolyzed. Specifically, the amine compound according to the present invention is easily converted into 3-[(4-dipropylaminobutyl)(4-{[(1H-imidazol-2-ylmethyl)(1-methyl-1H-imidazol-2-ylmethyl)amino]methyl}benzyl)amino]propionic acid through decomposition of the ester due to metabolism by the body of the subject. The amine compound according to the present invention thus exhibits excellent oral absorption properties, and is highly safe.

The amine compound according to the present invention has anti-HIV activity based on CXCR4 antagonism that is equivalent to that of the hydrolyzed compound. The amine compound according to the present invention thus exhibits an excellent therapeutic or preventive effect against various diseases (e.g., virus infection (e.g., HIV), rheumatism, and metastatic disease) based on the CXCR4 antagonism in addition to the above effects.

DESCRIPTION OF EMBODIMENTS

Prodrug

An amine compound according to one embodiment of the present invention is described below. The meaning of the term "prodrug" used herein and the significance of the present invention are briefly described below before describing the details of the amine compound.

The inventors conducted extensive studies in order to develop a novel compound that functions as an excellent CXCR4 antagonist. As a result, the inventors found a group of amine compounds, and sufficiently confirmed that these amine compounds have pharmacological activity (see Patent Documents 1 and 2, for example). Some of these amine compounds that do not exhibit excellent oral absorption properties are converted into a prodrug through esterification of the carboxyl group in order to improve oral absorption properties.

The term "prodrug" used herein is described below. Even a compound that exhibits high pharmacological activity may be decomposed in the digestive tract or the liver after administration, so that the amount of the active ingredient may decrease significantly. The prodrug was conceived in order to solve such a problem. Specifically, the term "prodrug" used herein refers to a compound that is chemically modified so that the compound is converted into a compound that exhibits pharmacological activity in vivo or after the compound has reached the target site, and the resulting compound exhibits its pharmacological effect (is activated). In other words, the term "prodrug" used herein refers to a precursor substance that is chemically or biochemically metabolized to function as an effective drug after administration.

Structure of Amine Compound

The amine compound according to the present invention is represented by the following general formula (2).

(2)

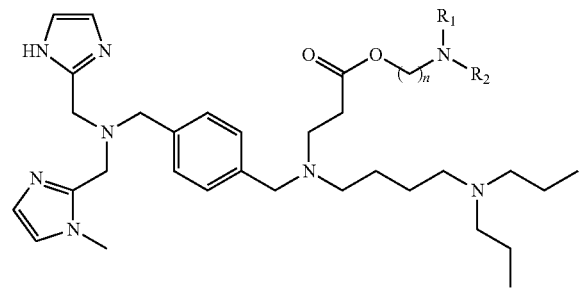

wherein n is an integer from 1 to 4, and $R_1$ and $R_2$ represent an alkyl group having 1 to 3 carbon atoms.

The amine compound is converted into a prodrug through chemical modification using various substituents. It is preferable to convert the amine compound into a prodrug through esterification of the carboxyl group in order to increase lipophilicity and improve oral absorption properties. The amine compound in which the carboxyl group is esterified is easily hydrolyzed due to the effects of an esterase present in the liver or the like, so that a pharmacologically active compound is obtained.

The amine compound according to the present invention is administered orally, and absorbed through the bowel wall. The amine compound is hydrolyzed and metabolically activated in the bowel wall or plasma due to an esterase from the liver or the like.

It is preferable that the amine compound according to the present invention is a dialkylamine ester. More specifically, it is preferable that the amine compound according to the present invention is an ester obtained by bonding the carboxyl group of 3-[(4-dipropylaminobutyl)(4-{[(1H-imidazol-2-ylmethyl)(1-methyl-1H-imidazol-2-ylmethyl)amino]methyl}benzyl)amino]propionic acid (see the following formula (3)) and the hydroxyl group of an alcohol represented by the following general formula (4) via an ester linkage.

(3)

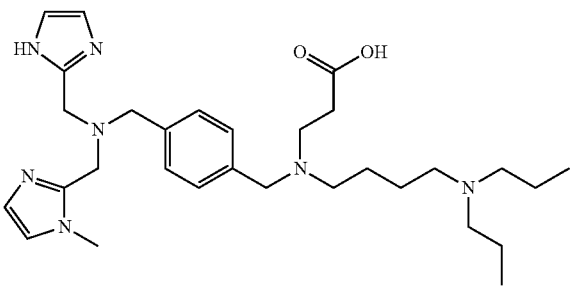

(4)

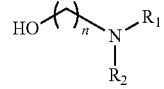

wherein n is an integer from 1 to 4, and $R_1$ and $R_2$ represent an alkyl group having 1 to 3 carbon atoms. n in the general formula (4) is preferably 2 or 3, and more preferably 2. $R_1$ in the general formula (4) preferably represents a methyl group or an ethyl group, and more preferably represents a methyl group. $R_2$ in the general formula (4) preferably represents a methyl group or an ethyl group, and more preferably represents a methyl group. $R_1$ and $R_2$ may be either identical or different. It is most preferable that both $R_1$ and $R_2$ represent a methyl group. The alkyl group having 1 to 3 carbon atoms may be either linear or branched.

Specifically, it is most preferable that the amine compound according to the present invention is an ester of 3-[(4-dipropylaminobutyl)(4-{[(1H-imidazol-2-ylmethyl)(1-methyl-1H-imidazol-2-ylmethyl)amino]methyl}benzyl)amino]propionic acid and 2-dimethylaminoethanol.

Details of Amine Compound

The details of the amine compound according to the present invention are described below.

Table 1 shows examples of the structural formula of the amine compound according to the present invention. The compounds are hereinafter specified using the compound number shown in Table 1. For example, a compound No. n (n=1 to 9) is indicated as a compound n (n=1 to 9). Though the compounds A and B shown in Table 1 do not fall under the amine compound according to the present invention, Table 1 shows the compounds A and B so that the features of the present invention can be more readily understood. The names of the compounds 1 to 9 and the compounds A and B are shown below.

Compound No. 1

2-dimethylaminoethyl 3-[(4-dipropylaminobutyl)(4-{[(1H-imidazol-2-ylmethyl)(1-methyl-1H-imidazol-2-ylmethyl)amino]methyl}benzyl)amino]propionate Compound No. 2

2-diethylaminoethyl 3-[(4-dipropylaminobutyl)(4-{[(1H-imidazol-2-ylmethyl)(1-methyl-1H-imidazol-2-ylmethyl)amino]methyl}benzyl)amino]propionate Compound No. 3

2-dipropylaminoethyl 3-[(4-dipropylaminobutyl)(4-{[(1H-imidazol-2-ylmethyl)(1-methyl-1H-imidazol-2-ylmethyl)amino]methyl}benzyl)amino]propionate Compound No. 4

2-dimethylaminopropyl 3-[(4-dipropylaminobutyl)(4-{[(1H-imidazol-2-ylmethyl)(1-methyl-1H-imidazol-2-ylmethyl)amino]methyl}benzyl)amino]propionate Compound No. 5

2-diethylaminopropyl 3-[(4-dipropylaminobutyl)(4-{[(1H-imidazol-2-ylmethyl)(1-methyl-1H-imidazol-2-ylmethyl)amino]methyl}benzyl)amino]propionate Compound No. 6

2-dipropylaminopropyl 3-[(4-dipropylaminobutyl)(4-{[(1H-imidazol-2-ylmethyl)(1-methyl-1H-imidazol-2-ylmethyl)amino]methyl}benzyl)amino]propionate Compound No. 7

2-dimethylaminobutyl 3-[(4-dipropylaminobutyl)(4-{[(1H-imidazol-2-ylmethyl)(1-methyl-1H-imidazol-2-ylmethyl)amino]methyl}benzyl)amino]propionate Compound No. 8

2-diethylaminobutyl 3-[(4-dipropylaminobutyl)(4-{[(1H-imidazol-2-ylmethyl)(1-methyl-1H-imidazol-2-ylmethyl)amino]methyl}benzyl)amino]propionate Compound No. 9

2-dipropylaminobutyl 3-[(4-dipropylaminobutyl)(4-{[(1H-imidazol-2-ylmethyl)(1-methyl-1H-imidazol-2-ylmethyl)amino]methyl}benzyl)amino]propionate Compound A 3-[(4-dipropylaminobutyl)(4-{[(1H-imidazol-2-ylmethyl)(1-methyl-1H-imidazol-2-ylmethyl)amino]methyl}benzyl)amino]propionic acid Compound B ethyl 3-[(4-dipropylaminobutyl)(4-{[(1H-imidazol-2-ylmethyl)(1-methyl-1H-imidazol-2-ylmethyl)amino]methyl}benzyl)amino]propionate

TABLE 1

| No. | Structural formula |
|---|---|
| 1 | |

TABLE 1-continued
| No. | Structural formula |
|---|---|
| 2 | 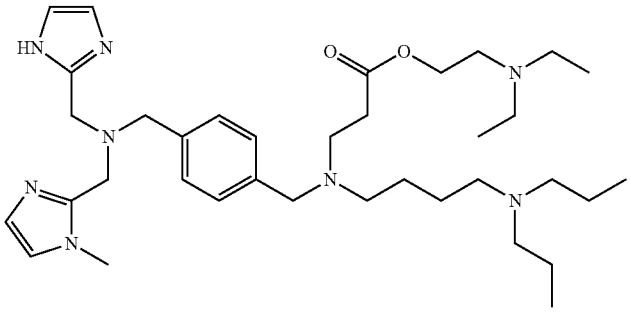 [SMILES: CCCN(CCC)CCCCN(CCC(=O)OCCN(CC)CC)Cc1ccc(CN(Cc2ncc[nH]2)Cc2nccn2C)cc1] |
| 3 | 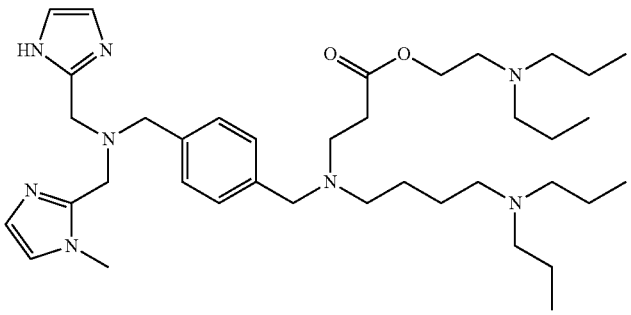 [SMILES: CCCN(CCC)CCCCN(CCC(=O)OCCN(CCC)CCC)Cc1ccc(CN(Cc2ncc[nH]2)Cc2nccn2C)cc1] |
| 4 | 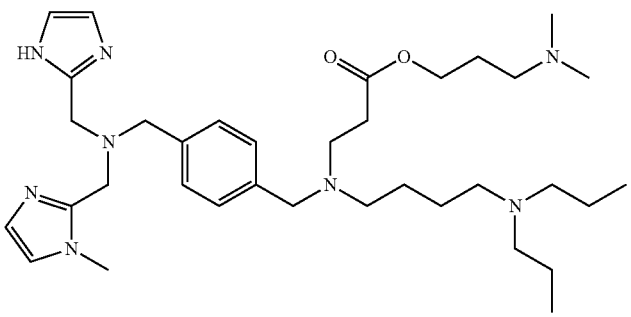 [SMILES: CCCN(CCC)CCCCN(CCC(=O)OCCCN(C)C)Cc1ccc(CN(Cc2ncc[nH]2)Cc2nccn2C)cc1] |
| 5 | 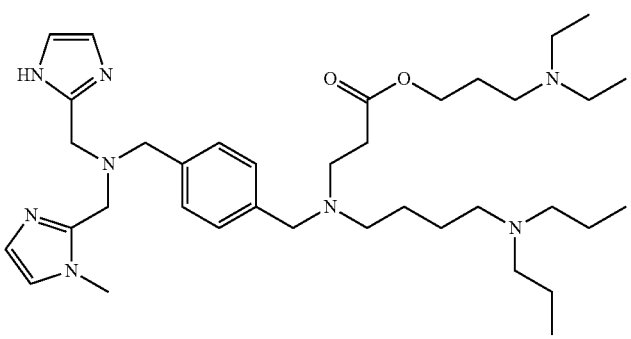 [SMILES: CCCN(CCC)CCCCN(CCC(=O)OCCCN(CC)CC)Cc1ccc(CN(Cc2ncc[nH]2)Cc2nccn2C)cc1] |

TABLE 1-continued

| No. | Structural formula |
|---|---|
| 6 | |
| 7 | |
| 8 | |
| 9 | |

TABLE 1-continued

| No. | Structural formula |
|---|---|
| A | (structure) |
| B | (structure) |

Form of Amine Compound

The amine compound according to the present invention may be in the form of a salt. The amine compound according to the present invention may be in the form of an arbitrary salt as long as the salt is a pharmacologically acceptable salt.

Examples of the pharmacologically acceptable salt include a trifluoroacetate, a hydrochloride, an acetate, a sulfate, a nitrate, a lactate, a maleate, a methanesulfonate, a toluenesulfonate, a tartrate, a citrate, an oxalate, a malonate, a succinate, a fumarate, a propionate, a butyrate, a salt of glucuronic acid, terephthalic acid, phosphoric acid, and the like. It is preferable that the pharmacologically acceptable salt is a hydrochloride, a maleate, a tartrate, or a citrate. Among them, a citrate is more preferable. The amine compound according to the present invention may form a hydrate or a solvate.

Properties of Amine Compound

The amine compound according to the present invention has anti-HIV activity based on CXCR4 antagonism. Specifically, the amine compound according to the present invention is a prodrug of the compound A, which serves as a pharmacologically active substance, and is a compound that has anti-HIV activity based on the CXCR4 antagonism.

The amine compound according to the present invention is also effective against other diseases that can be treated based on the CXCR4 antagonism. Examples of such diseases include rheumatism, metastatic diseases, and the like.

Pharmaceutical Preparation

The amine compound according to the present invention may be used as an active ingredient for a pharmaceutical preparation that is used to treat or prevent various diseases based on CXCR4 antagonism. The amine compound according to the present invention that is included in the pharmaceutical preparation may be further made chemical modification in part. Specifically, the pharmaceutical preparation may include a prodrug of the amine compound according to the present invention, serving as a pharmacologically active substance.

The prodrug, for example, may have such a structure: at least one functional group that is metabolized and eliminated in vivo is bonded to an arbitrary nitrogen atom that forms an arbitrary heterocyclic ring or chain of the amine compound represented by the general formula (2). Examples of the functional group include an alkoxycarbonyl group, a dialkylaminosulfone group, and the like.

The amine compound included as an active ingredient in the pharmaceutical preparation may be in the form of an above-mentioned pharmacologically acceptable salt.

The pharmaceutical preparation may include a pharmacologically acceptable carrier, a vehicle, a diluent, an extender, a disintegrator, a stabilizer, a preservative, a buffer, an emulsifier, a flavoring agent, a coloring agent, a sweetener, a viscous agent, a flavoring substance, a solubilizer, and the like in addition to the amine compound according to the present invention. Specific examples of such additives include water, vegetable oils, alcohols such as ethanol and benzyl alcohol, glycol, glycerol triacetate, gelatin, carbohydrates such as lactose and starch, magnesium stearate, potassium stearate, talc, lanolin, petroleum jelly, macrogol, crystalline cellulose, hydroxypropyl cellulose, and the like.

The dosage form of the pharmaceutical preparation is not particularly limited. Examples of the dosage form include a tablet, a powder, granules, a capsule, a pill, a suppository, an injection, eye drops, a liquid medicine, a lozenge, an aerosol, a suspension, an emulsion, medicated syrup, and the like.

The dosage of the pharmaceutical preparation differs depending on the type and the stage of disease, the compound to be administered, the route of administration, and the age, sex, and weight of the patient. In the general case of oral administration, the dosage preferably lies in the range of 0.1 to 5000 mg per adult, and more preferably in the range of 1 to 3000 mg per adult. In the case of the prodrug of the amine compound according to the present invention, serving as a pharmacologically active substance, the dosage preferably lies in the range of 1 to 5000 mg per adult.

The present invention is not limited to the above embodiments. Various modifications may be made to the above embodiments within the scope of the invention recited in the claims. A configuration achieved by appropriately combining the technical means disclosed in connection with the embodiments is also intended to be included within the technical scope of the present invention.

EXAMPLES

The present invention is further described below by way of examples. Note that the present invention is not limited to the following examples.
A production example of 2-dimethylaminoethyl 3-[(4-dipropylaminobutyl)(4-{[(1H-imidazol-2-ylmethyl)(1-methyl-1H-imidazol-2-ylmethyl)amino]methyl}benzyl)amino]propionate (compound No. 1 shown in Table 1 (hereinafter may be referred to as "compound 1")) is described below as Example 1. The compound 1 can be produced by utilizing a known organic chemical reaction. In the examples, a commercially available product (e.g., a product manufactured by Tokyo Chemical Industry Co., Ltd. (Tokyo) or Kanto Kagaku Co., Ltd. (Tokyo)) that is readily available for skilled persons was used as a reagent unless otherwise specified.

Example 1

Production Example 1

Synthesis of citrate of 2-dimethylaminoethyl 3-[(4-dipropylaminobutyl)(4-{[(1H-imidazol-2-ylmethyl)(1-methyl-1H-imidazol-2-ylmethyl)amino]methyl}benzyl)amino]propionate (compound 1)

Production Example 1-1

Synthesis of N-{4-[(benzylideneamino)methyl]benzyl}-N',N'-dipropylbutane-1,4-diamine 11.7 g (29.2 mmol) of N-(4-aminomethylbenzyl)-N',N'-dipropylbutane-1,4-diamine trihydrochloride was dissolved in distilled water, washed with toluene, adjusted to a pH of 11 using a sodium hydroxide aqueous solution, and extracted with toluene. The organic layer was dried over anhydrous sodium sulfate, concentrated, and dried under reduced pressure to obtain 8.07 g (27.7 mmol) of a free compound. The compound was dissolved in 81 ml of methanol, and the atmosphere inside the system was replaced with argon. 2.88 ml (1.02 eq) of benzaldehyde was added, followed by the addition of 5.63 ml (2.0 eq) of trimethyl orthoformate, and the mixture was stirred for 25 hours in an argon atmosphere. After completion of the reaction, the solvent was concentrated, and the residue was dried under reduced pressure to obtain 10.45 g of the target compound as a light yellow oily product (99.4%).
MS (Fab., Pos.): m/z=480 [M+H]$^+$
$^1$H-NMR (500 MHz, CDCl$_3$): δ=0.85 (6H, t, J=7.3 Hz), 1.23 (3H, t, J=7.1 Hz), 1.34-1.51 (8H, m), 2.30-2.36 (6H, m), 2.36-2.43 (2H, m), 2.45 (2H, t, J=7.3 Hz), 2.79 (2H, t, J=7.3 Hz), 3.55 (2H, s), 4.10 (2H, q, J=7.1 Hz), 4.81 (2H, s), 7.16-7.32 (4H, m), 7.41-7.43 (3H, m), 7.77-7.80 (2H, m), 8.40 (1H, s).

Production Example 1-2

Synthesis of ethyl 3-[{4-[(benzylideneamino)methyl]benzyl}-(4-dipropylaminobutyl)amino]propionate 10.45 g (27.5 mmol) of the compound synthesized in Production Example 1-1 was dissolved in 200 ml of acetonitrile, and the atmosphere inside the system was replaced with argon. 859 mg (5 mol %) of ytterbium trifluoromethanesulfonate and 6.02 ml (2.0 eq) of ethyl acrylate were added, and the mixture was stirred at room temperature for 92 hours. After completion of the reaction, the solvent was concentrated and 200 ml of toluene was added to the residue. The mixture was washed with a potassium carbonate aqueous solution (pH: 10). The aqueous layer was extracted again with 100 ml of toluene. The resulting organic layer was combined with the organic layer that was previously obtained, and the mixture was washed with distilled water and a saturated sodium chloride solution. The mixture was dried over anhydrous sodium sulfate, concentrated, azeotropically distilled with toluene, and dried under reduced pressure to obtain 13.13 g of the target compound as a light orange oily product (99.5%).

Production Example 1-3

Synthesis of ethyl 3-[(4-aminomethylbenzyl)(4-dipropylaminobutyl)amino]propionate 13.13 g (27.4 mmol) of the compound synthesized in Production Example 1-2 was dissolved in 39 ml of ethanol. 328 ml (12 eq) of a 1 mol/l hydrochloric acid aqueous solution was added dropwise over 30 minutes under cooling with ice, and the mixture was stirred at room temperature for 5 hours. After completion of the reaction, the solvent was concentrated, and the residue was washed with toluene and ethyl acetate. The pH of the mixture was adjusted to 9 using potassium carbonate, chloroform was added to the aqueous layer, and the resulting organic layer was washed with a saturated sodium chloride solution. The mixture was dried over anhydrous sodium sulfate, the solvent was evaporated, and the residue was dried under reduced pressure to obtain 9.84 g of the target compound as a colorless oily product (91.8%).

Production Example 1-4

Synthesis of ethyl 3-[(4-dipropylaminobutyl)(4-{[(1H-imidazol-2-ylmethyl)amino]methyl}benzyl)amino]propionate 9.14 g (23.3 mmol) of the compound synthesized in Production Example 1-3 was dissolved in 90 ml of ethanol. 2.35 g (1.05 eq) of 2-imidazolecarboaldehyde and 7.10 ml of trimethyl orthoformate were added, and the mixture was stirred at room temperature for 19 hours. The reaction system was then cooled in an ice bath. 1.32 g (1.5 eq) of sodium borohydride was added, and the mixture was stirred at room temperature for 2 hours.
After completion of the reaction, 20 ml of concentrated hydrochloric acid and 130 ml of distilled water were added to the mixture under cooling with ice, and the mixture was stirred to quench sodium borohydride. The mixture was neutralized by adding 34 g of potassium carbonate (pH: 10 to 11), and toluene was added to the mixture. The resulting organic layer was washed with distilled water and a saturated sodium chloride solution, and dried over anhydrous sodium sulfate. The solvent was then evaporated, and the residue was dried under reduced pressure, and dissolved in 200 ml of ethanol. 3.03 g (1.2 eq) of 1-methyl-2-imidazolecarboaldehyde and 11.65 g (2.4 eq) of sodium triacetoxyborohydride were added, and the mixture was stirred at room temperature for 3 days.

After completion of the reaction, the solvent was concentrated so that the amount was approximately halved, and the residue was slowly added to 300 ml of a saturated sodium hydrogen carbonate aqueous solution. Toluene was added, the resulting organic layer was washed with a saturated sodium chloride solution, dried over anhydrous sodium sulfate, and the solvent was evaporated. The residue was purified by silica gel column chromatography (Chromatorex NH: 250 g, chloroform/acetonitrile=2/1) to obtain 10.05 g of the target compound as a colorless oily product (77.6%).

Production Example 1-5

Synthesis of 3-[(4-dipropylaminobutyl)(4-{[(1H-imidazol-2-ylmethyl)(1-methyl-1H-imidazol-2-ylmethyl)amino]methyl}benzyl)amino]propionic acid 4.71 g (8.32 mmol) of the compound synthesized in Production Example 1-4 was dissolved in 47 ml of methanol, 16.6 ml (2 eq) of a 1 mol/l sodium hydroxide aqueous solution was added, and the mixture was stirred at room temperature for 4 hours. After completion of the reaction, the solution was concentrated, and 16.6 ml of 1 mol/l hydrochloric acid was added to the mixture. Sodium chloride was added so that saturation occurred, and then chloroform was added to the mixture. The resulting organic layer was washed with a saturated sodium chloride solution and dried over anhydrous sodium sulfate, and the solvent was evaporated. The residue was dried under vacuum to obtain 3.44 g of the target compound as a colorless viscous liquid (76.9%).

Production Example 1-6

Synthesis of 2-dimethylaminoethyl 3-[(4-dipropylaminobutyl)(4-{[(1H-imidazol-2-ylmethyl)(1-methyl-1H-imidazol-2-ylmethyl)amino]methyl}benzyl)amino]propionate (compound 1)

0.250 ml (2-fold amount) of dimethylaminoethanol was added to 114.4 mg (0.213 mmol) of the compound synthesized in Production Example 1-5, and the mixture was mixed thoroughly. 1.1 ml of a 4 mol/l hydrogen chloride/dioxane solution was added carefully, and the mixture was stirred at room temperature for 20 hours. After completion of the reaction, the solvent was concentrated, and water was added to the mixture. The mixture was washed with ethyl acetate, and the pH of the mixture was adjusted to 9 using a sodium hydroxide aqueous solution. Ethyl acetate was added to the aqueous layer, and the resulting organic layer was washed with a saturated sodium chloride solution and dried over anhydrous sodium sulfate. The solvent was evaporated, and the residue was purified by silica gel column chromatography (Chromatorex NH, chloroform/acetonitrile=1/1) to obtain 81.2 mg of the target compound as a colorless viscous liquid (62.6%).

MS (Fab., Pos.): m/z=609 [M+H]$^+$ $^1$H-NMR (500 MHz, CDCl$_3$): δ=0.85 (6H, t, J=7.3 Hz), 1.35-1.48 (8H, m), 2.26 (6H, s), 2.26-2.39 (6H, m), 2.42 (2H, t, J=7.6 Hz), 2.47-2.54 (4H, m), 2.79 (2H, t, J=7.6 Hz), 3.46 (2H, s), 3.55 (5H, s), 3.62 (2H, s), 3.67 (2H, s), 4.14 (2H, t, J=5.6 Hz), 6.87 (1H, d, J=1.2 Hz), 6.99 (1H, d, J=1.2 Hz), 7.08 (1H, brs), 7.12 (1H, brs), 7.26 (2H, d, J=8.1 Hz), 7.32 (2H, d, J=8.1 Hz), 12.35 (1H, brs).

Production Example 1-7

Synthesis of citrate of 2-dimethylaminoethyl 3-[(4-dipropylaminobutyl)(4-{[(1H-imidazol-2-ylmethyl)(1-methyl-1H-imidazol-2-ylmethyl)amino]methyl}benzyl)amino]propionate (compound 1)

0.5 ml of acetone was added to 88.2 mg (0.420 mmol) of citric acid hydrate, and 0.5 ml of an acetone solution of 101.2 mg (0.166 mmol) of the compound synthesized in Production Example 1-6 was added dropwise to the mixture with stirring. 1.5 ml of acetone was added, and the mixture was stirred at room temperature for 40 minutes. The mixture was then subjected to decantation, and the resulting solid was washed three times with 4 ml of acetone. The solid was dried under reduced pressure to obtain a citrate of the compound 1 as a white solid (181.3 mg (100%)).

$^1$H-NMR (500 MHz, DMSO-d$_6$): δ=0.88 (6H, t, J=7.3 Hz), 1.40-1.47 (2H, m), 1.35-1.48 (8H, m), 2.35-2.42 (2H, m), 2.38 (6H, s), 2.54 (5H, d, J=15.2 Hz), 2.62 (5H, d, J=15.2 Hz), 2.67-2.70 (2H, m), 2.76-2.78 (2H, m), 2.88-2.91 (6H, m), 3.51-3.55 (9H, m), 3.59 (2H, s), 4.15 (2H, t, J=5.6 Hz), 6.84 (1H, d, J=1.2 Hz), 7.03 (2H, s), 7.11 (1H, d, J=1.2 Hz), 7.23 (2H, d, J=8.1 Hz), 7.32 (2H, d, J=8.1 Hz).

In Example 2, the amine compound according to the present invention was subjected to an anti-HIV activity test and a hydrolysis test.

Example 2

Test Example 1

In Test Example 1, the amine compound according to the present invention was subjected to the anti-HIV activity test. The compounds 1, A, and B shown in Table 1 were used.

HIV-1 IIIB infected MT-4 cells (3.0×10$^4$ cells/well, MOI (multiplicity of infection): 0.01) were added to a 96-well microtiter plate together with the test compound (compound 1, A, or B) at a different concentration immediately after infection. After culturing the cells at 37° C. for 5 days using a carbon dioxide incubator, the number of viable cells was measured by the MTT (tetrazolium) method (Pawels et al., J. Virol. Method, 20, 309-321, 1988). The results are shown in Table 2.

TABLE 2

| Compound No. | EC50 (μM) |
|---|---|
| 1 | 0.003 |
| A | 0.003 |
| B | 0.003 |

Test Example 2

In Test Example 2, the compound 1 was subjected to the hydrolysis test. The compound 1 that is an ester is hydrolyzed to the compound A.

147 μl of a human serum pool (Cosmo Bio Co., Ltd.) or a pooled serum obtained by centrifuging (3500 rpm×10 min) whole blood collected from a Crj:CD (SD) IGS male rat (Charles River Laboratories Japan, Inc.) was dispensed to a tube. 147 μl of a physiological saline solution (Hikari Pharmaceutical Co., Ltd.) was dispensed to the tube, and the mixture was preincubated for 3 minutes. 3 μl of a solution (concentration: 500 μmol/l) that was prepared by diluting a 25 mmol/l DMSO solution of the compound 1 with a physiological saline solution was added, and the components were mixed. The mixture was reacted for 30 minutes using a thermomixer. 600 μl of a 0.1% formic acid/methanol solution was added, and the components were mixed. The mixture was then centrifuged (15000 rpm×5 min), and the supernatant liquid was subjected to liquid chromatography-mass spectrometry (LCMS). It was confirmed that the compound 1 had been converted into the compound A. The conversion rate (%) into the compound A is shown in Table 3.

TABLE 3

| Compound | Human | | Rat | |
|---|---|---|---|---|
| No. | 0 min | 30 min | 0 min | 30 min |
| 1 | 0% | 113% | 0% | 90% |

It was confirmed by Test Example 1 that the compound 1 had an EC50 of 0.003 μM, and exhibited anti-HIV activity equivalent to that of the compounds A and B. EC50 is the concentration (50% effective concentration) at which cellular damage due to HIV infection is inhibited by 50%.

It was confirmed by Test Example 2 that the compound 1 was converted into the compound A at a conversion rate of about 100% when using both human serum and rat serum. It was thus confirmed the compound 1 is easily hydrolyzed in human serum, and is highly safe when administered to a human subject.

INDUSTRIAL APPLICABILITY

The amine compound according to the present invention may suitably be used as an active ingredient of a pharmaceutical preparation that is used to treat or prevent various diseases based on CXCR4 antagonism.

The invention claimed is:

1. An amine compound represented by a general formula (1) or a pharmacologically acceptable salt thereof, (1)

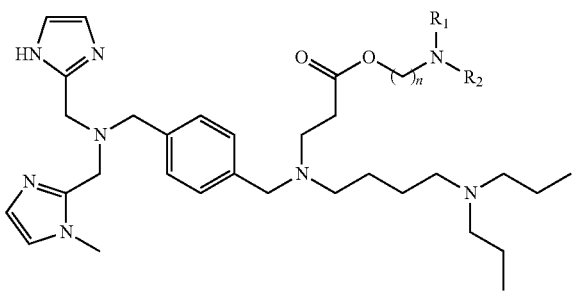

wherein n is an integer from 1 to 4, and $R_1$ and $R_2$ represent an alkyl group having 1 to 3 carbon atoms.

2. An amine compound or a pharmacologically acceptable salt thereof according to claim 1, wherein n in the general formula (1) is 2 or 3.

3. An amine compound or a pharmacologically acceptable salt thereof according to claim 2, wherein n in the general formula (I) is 2, and $R_1$ and $R_2$ in the general formula (1) represent a methyl group or an ethyl group.

4. An amine compound or a pharmacologically acceptable salt thereof according to claim 1, wherein the amine compound represented by the general formula (1) is 2-dimethylaminoethyl 3-[(4-dipropylaminobutyl)(4-{[(1H-imidazol-2-ylmethyl)(1-methyl-1H-imidazol-2-ylmethyl)amino]methyl}benzyl)amino]propionate.

5. An amine compound or a pharmacologically acceptable salt thereof according to claim 4, wherein the pharmacologically acceptable salt is a citrate of 2-dimethylaminoethyl 3-[(4-dipropylaminobutyl)(4-{[(1H-imidazol-2-ylmethyl)(1-methyl-1H-imidazol-2-ylmethyl)amino]methyl}benzyl)amino]propionate.

6. A pharmaceutical composition comprising as an active ingredient the amine compound or the pharmacologically acceptable salt thereof according to claim 1.

7. A pharmaceutical composition according to claim 6, comprising as a prodrug the amine compound or the pharmacologically acceptable salt thereof according to claim 1.

8. A CXCR4 antagonist comprising as an active ingredient the amine compound or the pharmacologically acceptable salt thereof according to claim 1.

9. An antiviral drug comprising as an active ingredient the amine compound or the pharmacologically acceptable salt thereof according to claim 1.

10. An anti-rheumatic disease agent based on CXCR4 antagonism, the anti-rheumatic disease agent comprising as an active ingredient the amine compound or the pharmacologically acceptable salt thereof according claim 1.

11. An anti-metastatic disease agent based on CXCR4 antagonism, comprising as an active ingredient the amine compound or the pharmacologically acceptable salt thereof according to claim 1.

\* \* \* \* \*

UNITED STATES PATENT AND TRADEMARK OFFICE
CERTIFICATE OF CORRECTION

PATENT NO.         : 8,722,719 B2
APPLICATION NO.    : 13/878131
DATED              : May 13, 2014
INVENTOR(S)        : R. Matsui et al.

Page 1 of 1

It is certified that error appears in the above-identified patent and that said Letters Patent is hereby corrected as shown below:

In the claims, column 18, line 44 (claim 10, line 4), please change "according claim 1." to --according to claim 1.--.

Signed and Sealed this
Twenty-third Day of September, 2014

Michelle K. Lee
*Deputy Director of the United States Patent and Trademark Office*